United States Patent
Reisinger et al.

(10) Patent No.: US 6,469,191 B1
(45) Date of Patent: Oct. 22, 2002

(54) METHOD FOR PRODUCING DIARYL CARBONATES

(75) Inventors: Claus-Peter Reisinger, Krefeld; Ursula Jansen, Neuss, both of (DE); Johann Rechner, Kapellen (BE); Rob Eek, Bergen op Zoom (NL)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/868,558

(22) PCT Filed: Dec. 9, 1999

(86) PCT No.: PCT/EP99/09696

§ 371 (c)(1),
(2), (4) Date: Jun. 19, 2001

(87) PCT Pub. No.: WO00/37413

PCT Pub. Date: Jun. 29, 2000

(30) Foreign Application Priority Data

Dec. 22, 1998 (DE) .......................................... 198 59 290

(51) Int. Cl.$^7$ .............................................. C07C 69/96
(52) U.S. Cl. ...................................................... 558/260
(58) Field of Search .......................................... 558/274

(56) References Cited

U.S. PATENT DOCUMENTS

| 4,201,712 | A | | 5/1980 | Weber et al. ............. 260/244.4 |
|---|---|---|---|---|
| 5,498,724 | A | | 3/1996 | Nyström et al. ......... 548/375.1 |
| 5,498,742 | A | | 3/1996 | Buyseh et al. ............... 558/274 |
| 5,874,605 | A | * | 2/1999 | Yoshida et al. ............. 558/274 |
| 5,900,501 | A | * | 5/1999 | Ooms et al. ................ 558/274 |
| 6,093,842 | A | * | 7/2000 | Oyevaar et al. ............ 558/274 |
| 6,294,684 | B1 | * | 9/2001 | de Bruin et al. ............ 558/274 |
| 6,350,893 | B1 | * | 2/2002 | Ritzer et al. ................ 558/275 |

FOREIGN PATENT DOCUMENTS

| EP | 0 749 955 | 12/1996 |
|---|---|---|
| EP | 0 801 051 | 10/1997 |

* cited by examiner

*Primary Examiner*—Deborah C. Lambkin
(74) *Attorney, Agent, or Firm*—Joseph C. Gil; Aron Preis

(57) ABSTRACT

A process for the production of an aromatic carbonate is disclosed. Accordingly, an aromatic hydroxy compound is reacted with carbon monoxide and oxygen in the presence of a platinum group metal catalyst, a co-catalyst, a base, and optionally a quaternary salt as well as an inert organic solvent. The reaction is carried out under conditions whereby the inert organic solvent forms an azeotrope with the water arising during the reaction. The azeotrope is then removed from the reaction mixture.

12 Claims, No Drawings

METHOD FOR PRODUCING DIARYL CARBONATES

This application is a 371 of PCT/EP99/09696 filed Dec. 12, 1999.

It is known to produce organic carbonates by oxidative reaction of an aromatic hydroxy compound with carbon monoxide in the presence of a noble metal catalyst (DE-OS 27 38 437). Palladium is preferably used as the noble metal. A co-catalyst (for example manganese or cobalt salts), a base, a quaternary salt, various quinones or hydroquinones and desiccants may additionally be used. The process may be performed in a solvent, preferably methylene chloride.

When reacting aromatic dihydroxy compounds with carbon monoxide and oxygen, one mole of water is liberated per mole of carbonate units formed. If this water remains in the reaction system, organic carbonate which has already been formed may be hydrolysed, such that the space-time yields which may be achieved without effective water separation are only low; the catalyst system may moreover be deactivated by water. However, reactivation of the deactivated catalyst entails considerable technical effort. Replacing the deactivated catalyst with fresh catalyst is very costly. Effective removal of water is consequently essential for economic use of this process.

DE-OS 27 38 437 proposes using molecular sieve for separating water. However, using molecular sieve makes industrial use of the process unattractive as effective separation of the water from the liquid phase entails using large quantities of molecular sieve (100–500% excess) which must be regenerated in a technically elaborate manner.

U.S. Pat. No. 5,498,724 discloses a process in which the water formed during the reaction is removed by stripping with excess reaction gas. The reaction gas may contain 0 to 30vol. % of an inert gas which forms an azeotrope with water. The reaction mixture may also contain inert organic solvents. However, large quantities of gas must be used in this process in order to remove the water completely; the minimum achievable water content is above 500 ppm. When the water is removed, relatively large quantities of aromatic hydroxy compound are also discharged, which must be separated from the gas stream.

It has now surprisingly been found that adding inert organic solvents to the reaction mixture, which solvents form an azeotrope with water under the reaction conditions, and removing this azeotrope from the reaction mixture, makes it possible to adjust the water content in the reaction mixture to distinctly below 500 ppm, preferably even below 250 ppm. Substantially smaller quantities of reaction gas may additionally be used than when performing pure stripping with reaction gas (DE-OS 44 03 075). Considerable cost savings may accordingly be made when implementing the process on a large industrial scale.

The present invention accordingly provides a process for the production of an aromatic carbonate of the formula

R—O—CO—O—R  (I), in which
R means a substituted or unsubstituted $C_6$–$C_{12}$ aryl, preferably substituted or unsubstituted phenyl, particularly preferably unsubstituted phenyl,
by reacting an aromatic hydroxy compound of the formula

R—O—H  (II), in which R has the above-stated meaning,
with carbon monoxide and oxygen in the presence of a platinum group metal catalyst, a co-catalyst, a base, and optionally a quaternary salt as well as an inert organic solvent, wherein, under the reaction conditions, the inert organic solvent forms an azeotrope with the water arising during the reaction, and this azeotrope is removed from the reaction mixture.

In a preferred embodiment, removal of the water from the reaction mixture as an azeotrope with the solvent is promoted by stripping with excess reaction gas. It is crucial in this process that more than 5 vol. % of the solvent are removed from the reaction mixture as an azeotrope. In a preferred embodiment, removal of the azeotrope from the reaction mixture is promoted by excess reaction gas. Distinctly lower conversions are achieved under pure stripping conditions (DE-OS 44 03 075), i.e. without formation of an azeotrope with the inert, organic solvent and simultaneous removal of the azeotrope from the reaction mixture.

The process according to the invention for forming carbonate is performed at a reaction temperature of 30 to 200° C., preferably of 50 to 150° C., particularly preferably of 60 to 130° C., and at a reaction pressure of 1 to 100 bar, preferably of 1 to 50 bar, particularly preferably of 1 to 10 bar. The temperature and total pressure should be selected such that the azeotrope may be formed under the reaction conditions and partially removed from the reaction mixture.

Halogenated hydrocarbons and aromatic solvents which boil at a suitable temperature and form azeotropes with water, such as chlorobenzene, dichlorobenzene, fluorobenzene, benzene, anisole, methylene chloride or 1,2-dichloroethane, optionally also mixtures thereof, may be used as the inert organic solvent. Chlorobenzene is particularly preferably used. The inert solvent may be present in the reaction mixture in a proportion of 1–99%, preferably of 20–98%, particularly preferably of 40–98%.

By means of a separating unit, such as for example a dephlegmator, a distillation column with plates or packing and other apparatus known to the person skilled in the art, located in the exhaust gas stream containing the azeotrope, the majority of the solvent entrained during dewatering may be separated from the water and passed into the return stream to the reactor. Separation or breaking of the separated azeotrope may be achieved in accordance with the prior art, for example by extraction, freezing or distillation.

In a preferred embodiment, the fraction of dissolved gases driven off with the azeotrope may be returned, once separated, to the circulating reactor gas. Entrained educts (for example phenol), solvents, products and water are separated from the gas mixture to be recycled, which is optionally compressed before separation, using prior art methods, for example by adsorption, absorption or preferably by condensation. The reaction gas required for the reaction, consisting of carbon monoxide, oxygen and an inert gas, is introduced to this end in a quantity of 1 to 10000 Nl per liter of reaction solution, preferably of 5 to 5000 Nl per liter of reaction solution and particularly preferably of 10 to 1000 Nl per liter of reaction solution. The gas mixture to be recycled originating from dewatering is included in the stated volume with regard to its content of CO and $O_2$.

The composition of the reaction gases carbon monoxide and oxygen may be varied within wide concentration limits, but a $CO:O_2$ molar ratio (standardised to CO) of 1:(0.001–1.0), preferably of 1:(0.01–0.5) and particularly preferably of 1:(0.02–0.3) is conveniently established. At these molar ratios, the oxygen partial pressure is sufficiently high to be able to achieve elevated space-time yields, while simultaneously avoiding explosive carbon monoxide/oxygen gas mixtures.

All the starting compounds may be contaminated with impurities from the production and storage thereof, but for the purposes of purity of the final product it is desirable to use the cleanest possible chemicals. No particular purity requirements apply to the reaction gases either. Synthesis gas may accordingly be used as the CO source and air as the $O_2$ medium, but care must be taken not to introduce any catalyst poisons such as for example sulfur or the compounds thereof. Pure CO and pure oxygen are used in the preferred embodiment of the process according to the invention.

Aromatic hydroxy compounds which may be reacted according to the invention comprise, for example, phenol, o-, m- or p-cresol, o-, m- or p-chlorophenol, o-, mor p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and bisphenol A, preferably phenol. In general, any substitution of the aromatic hydroxy compound comprises 1 or 2 substituents of the meaning $C_1$–$C_4$ alkyl, $C_1$–$C_4$ alkoxy, fluorine, chlorine or bromine.

Bases usable in the process according to the invention comprise alkali metal hydroxides, alkali metal salts or quaternary salts of weak acids such as alkali metal tert.-butylates or alkali metal salts or quaternary salts of aromatic hydroxy compounds of the formula (II), in which R has the above-stated meaning. It is very particularly preferred to use an alkali metal salt or quaternary salt of the aromatic hydroxy compound of the formula (II) which is also to be reacted to yield the organic carbonate, for example tetrabutylammonium phenolate. These alkali metal salts may be lithium, sodium, potassium, rubidium or caesium salts. Lithium, sodium and potassium phenolates are preferably used, with potassium phenolate being particularly preferred.

The base is added in catalytic quantities. The ratio of platinum group metal, for example palladium, to base is preferably selected such that 0.1 to 500, preferably 0.3 to 200, particularly preferably 0.9 to 130 equivalents of base are used per gram atom of platinum group metal, for example palladium.

The platinum group metal catalysts suitable for the process according to the invention consist of at least one group VIII noble metal, preferably palladium. It may added in various forms to the process according to the invention. Palladium may be used in metallic form or preferably in the form of palladium compounds of oxidation states 0 and +2, such as for example palladium(II) acetylacetonate, halides, carboxylates of $C_2$–$C_{18}$ carboxylic acids, nitrate, oxides or palladium complexes, which may, for example, contain olefins, amines, phosphorus compounds and halides. Palladium bromide and palladium acetylacetonate are particularly preferred.

There is no restriction on the quantity of platinum group metal catalyst in the process according to the invention. The catalyst is preferably added in a quantity such that the concentration of the metal in the reaction mixture is 1–3000 ppm, with concentrations of 5–500 ppm being particularly preferred.

A metal from groups III A, III B, IV A, IV B, V B, I B, II B, VI B, VII B, from the rare earth metals (atomic numbers 58–71) or the iron group of the (Mendeleyev) periodic system of elements, optionally also mixtures thereof, is/are used as the co-catalyst for the process according to the invention, wherein the metal may be used in different oxidation states. Mn, Cu, Co, V, Zn, Ce and Mo are preferably used. Without restricting the process according to the invention, manganese(II), manganese(III), copper(I), copper(II), cobalt(II), cobalt(III), vanadium(III) and vanadium(IV) may be mentioned. The metals may be used, for example, as halides, oxides, carboxylates of $C_2$–$C_6$ carboxylic acids, diketonates or nitrates, also as complex compounds, which may, for example, contain carbon monoxide, olefins, amines, phosphorus compounds and halides. Mn, Cu, Mo and Ce are particularly preferably used. Manganese compounds are very particularly preferably used in the process according to the invention, particularly preferably manganese(II) and manganese(III) complexes, very particularly preferably manganese(II) acetylacetonate or manganese(III) acetylacetonate.

The co-catalyst, which may also be formed in situ, is added in a quantity such that the concentration thereof is in the range from 0.0001 to 20 wt. % of the reaction mixture, with the concentration range preferably being from 0.005 to 5 wt. %, particularly preferably from 0.01 to 2 wt. %.

The quaternary salts used for the purposes of the present invention may, for example, comprise ammonium, guanidinium, phosphonium or sulfonium salts substituted with organic residues, optionally also mixtures thereof. Ammonium, guanidinium, phosphonium and sulfonium salts bearing $C_6$–$C_{10}$ aryl, $C_7$ to $C_2$ aralkyl and/or $C_1$ to $C_{20}$ alkyl residues as the organic residues and a halide, tetrafluoroborate or hexafluorophosphate as the anion are suitable for use in the process according to the invention. Ammonium salts which are preferably used in the process according to the invention are those which bear $C_6$–$C_{10}$ aryl, $C_7$ to $C_{12}$ aralkyl and/or $C_1$ to $C_{20}$ alkyl residues as the organic residues and a halide as the anion, with tetrabutylammonium bromide and tetrabutylphosphonium bromide being particularly preferred. The quantity of such a quaternary salt may, for example, be from 0.1–20 wt. %, relative to the weight of the reaction mixture. This quantity preferably amounts to 0.5–15 wt. %, particularly preferably from 1–5 wt. %.

When a base such as tetrabutylammonium phenolate, which contains a quaternary cation, is used, the quantity of added quaternary salt such as tetrabutylammonium bromide may be reduced accordingly. The total quantity of the anion of the added quaternary salt may optionally also be offset by other salts of this anion, such as potassium bromide.

In another embodiment, heterogeneous catalysts, in which the platinum group metal or the platinum group metal and the co-catalyst is/are applied onto a heterogeneous support, are used as powders or shapes instead of the homogeneous catalyst system. The remaining components of the catalyst system, such as the base, the quaternary compound and optionally the co-catalyst, are still homogeneously dissolved in the reaction solution. The quantity of the platinum group metal in the total weight of the heterogeneous catalyst is 0.01 to 15 wt. %, preferably from 0.05 to 10 wt. %, calculated as platinum group metal.

At least one metal compound of the above-stated type is used as co-catalyst on the catalyst support.

The quantity of the co-catalyst in the total weight of the heterogeneous catalyst is 0.01 to 15 wt. %, preferably 0.05 to 10 wt. %, calculated as metal. Suitable catalyst supports comprise one or more metal oxides from the group of V, Mn, Ti, Cu, Zr, La, the rare earth metals (atomic numbers 58–71), both as chemically uniform pure substances and as mixtures, as well as oxides of iron and cobalt, oxides of nickel, aluminium, silicon and magnesium, zeolites and activated carbons. When the supported catalyst is used as a powder, in order to ensure mixing of the reaction components, the stirred vessel to be used is equipped with agitators suitable for this purpose or is arranged as a bubble column reactor.

When using supported catalyst powders as a suspension in stirred vessels or bubble columns, the supported catalyst powder is used in quantities of 0.001 to 50 wt. %, preferably of 0.01 to 20 wt. %, particularly preferably of 0.1 to 10 wt. %, relative to the quantity of aromatic hydroxy compound used.

In preferred embodiments, the heterogeneous supported catalyst is used in immobilised form in stirred vessels, a bubble column, a trickle-bed reactor or cascades of these reactors. It is then possible completely to dispense with separation of the supported catalyst.

Suitable reactors for the process according to the invention using homogeneous or heterogeneous catalyst are stirred-tank reactors, autoclaves and bubble columns, wherein these reactors may be used individually or as cascades. A cascade may comprise 2 to 15, preferably 2 to 10, particularly preferably 2 to 5 reactors connected in series.

The stirred vessels to be used according to the invention are equipped with suitable agitators for mixing the reaction components. Such agitators are known to the person skilled in the art. The following may be mentioned by way of example: disk, impeller, propeller, turbine, MIG and Internig agitators, tubular agitators and various types of hollow agitators. Preferred agitators are those which permit effective mixing of gases and liquids, for example hollow tube sparging agitators, propeller agitators etc.

The following types of bubble columns may be used in the process according to the invention: simple bubble columns, bubble columns with internal fittings, such as for example bubble columns with parallel chambers, cascade bubble columns with sieve plates or single-hole plates, bubble columns with packings, with static mixers, pulsed flow sieve plate bubble columns, loop reactors, such as for example air-lift loop reactors, downflow loop reactors, jet loop reactors, open jet reactors, jet nozzle reactors, bubble columns with immersed fluid jets, downflow/upflow bubble columns and further bubble column reactors known to the person skilled in the art (*Chem. Ing. Tech.* 51 (1979), no. 3, pages 208–216; W.-D. Deckwer, *Reaktionstechnik in Blasensäulen*, Otto Salle Verlag 1985).

In a preferred embodiment, bubble column reactors and bubble column cascades are used which permit effective mixing of gas and liquid, such as for example cascade bubble columns and loop reactors. In order to maintain effective mixing of liquid and reaction gas, dispersion and redispersion elements may be arranged along the longitudinal axis of the bubble column reactors. Single hole plates, perforated plates, sieve plates and further internal fittings known to the person skilled in the art are used as fixed redispersion elements. Initial dispersion of the reaction gas in the liquid phase on feeding may be achieved by using conventional devices such as porous sintered plates, perforated plates, sieve plates, submerged tubes, nozzles, annular spargers and further dispersion devices known to the person skilled in the art.

The process according to the invention may be performed in various embodiments. One option is discontinuous operation. In this case, CO and oxygen are passed into the reaction mixture either through a sparging agitator, as in the case of a stirred-tank reactor or through other known gas dispersion elements. Once optimum conversion has been achieved, the reaction mixture is removed from the reactor or optionally worked up in the reactor. Where pulverulent supported catalysts are used, these may be separated from the reaction mixture for example by filtration, settling or centrifugation.

In the case of identical starting materials, supported catalysts used in discontinuous testing may be reused repeatedly, optionally without purification. In the case of continuous operation, the supported catalysts used may remain in the reactor over an extended period and optionally be regenerated.

Continuous operation in a single reactor or cascade of two or more reactors is preferably used. When immobilised heterogeneous catalysts are used, they may remain in the reactor over an extended period and optionally also be regenerated therein.

EXAMPLES

Example 1

0.3 mmol of palladium bromide, 22 mmol of tetrabutylammonium bromide and 20 g of phenol in 90 ml of chlorobenzene were initially introduced into a 250 ml autoclave with a sparging agitator, cooler and downstream cold trap and dissolved for 30 minutes at 90° C. with introduction of carbon monoxide (3 l/h). 2.2 mmol of manganese(III) acetylacetonate and 10.4 mmol of tetrabutylammonium phenolate were then added with 10 ml of chlorobenzene and the reaction started at a total pressure of 3 bar and 110° C. while 80 Nl/h of a gas mixture of carbon monoxide and oxygen (95:5 vol. %) were introduced. A sample was taken from the reaction mixture hourly and analysed by gas chromatography. The analyses revealed that 11.4% of diphenyl carbonate were present in the reaction mixture after only 1 hour and a total of 14.6% after 2 hours. 12 g of a chlorobenzene/water suspension had condensed in the cold trap. After completion of the test, the reaction mixture had a residual water content of less than 250 ppm.

Example 2

0.15 mmol of palladium bromide, 11 mmol of tetrabutylammonium bromide and 10 g of phenol in 90 ml of chlorobenzene were initially introduced into a 250 ml autoclave with a sparging agitator, cooler and downstream cold trap and dissolved for 30 minutes at 90° C. with introduction of carbon monoxide (3 l/h). 1.1 mmol of manganese(II) acetylacetonate and 5.2 mmol of potassium phenolate were then added with 10 ml of chlorobenzene and the reaction was started at a total pressure of 5 bar and 125° C. while 80 Nl/h of a gas mixture of carbon monoxide and oxygen (95:5 vol. %) were introduced. A sample was taken from the reaction mixture half-hourly and analysed by gas chromatography. The analyses revealed that 5.4% of diphenyl carbonate were present in the reaction mixture after 0.5 hour and a total of 7.2% after 1 hour. 10 g of a chlorobenzene/water suspension had condensed in the cold trap. After completion of the test, the reaction mixture had a residual water content of less than 250 ppm.

Example 3
(Comparison)

0.15 mmol of palladium bromide, 11 mmol of tetrabutylammonium bromide and 10 g of phenol in 90 ml of chlorobenzene were initially introduced into a 250 ml autoclave with a sparging agitator, cooler and downstream cold trap and dissolved for 30 minutes at 90° C. with introduction of carbon monoxide (3 l/h). 1.1 mmol of manganese(III) acetylacetonate and 5.2 mmol of potassium phenolate were then added with 10 ml of chlorobenzene and the reaction was started at a total pressure of 10 bar and 125° C. while 80 Nl/h of a gas mixture of carbon monoxide and oxygen (95:5 vol. %) were introduced. A sample was taken from the reaction mixture half-hourly and analysed by gas chromatography. The analyses revealed that 0.9% of diphenyl carbonate were present in the reaction mixture after 0.5 hour and a total of 1.2% after 1 hour. Less than 2 g of water had condensed in the cold trap. After completion of the test, the reaction mixture had a residual water content of greater than 500 ppm. The pressure and temperature used correspond to pure stripping conditions, as the azeotrope was hardly removed from the reaction mixture at all. The direct comparison with Example 2 demonstrates the efficiency with which the azeotrope is removed from the reaction mixture.

What is claimed is:

1. A process for the production of an aromatic carbonate of the formula $$R\text{—}O\text{—}CO\text{—}O\text{—}R \qquad (I),$$

in which

R means a substituted or unsubstituted $C_6$–$C_{12}$ aryl comprising reacting an aromatic hydroxy compound of the formula $$R\text{—}O\text{—}H \qquad (II),$$

which

R has the above-stated meaning,
with carbon monoxide and oxygen in the presence of a platinum group metal catalyst, a co-catalyst, a base, and optionally a quaternary salt as well as an inert organic solvent under conditions whereby the inert organic solvent forms an azeotrope with the water arising during the reaction, and removing said azeotrope from the reaction mixture.

2. The process of claim 1 wherein R denotes substituted or unsubstitutedphenyl.

3. The process of claim 1 wherein R denotes unsubstituted phenyl.

4. The process of claim 1 wherein said base is a member selected from the group consisting of alkali metal salt and quaternary salt of a weak acid.

5. Process according to claim 1, in which removal of the azeotrope from the reaction mixture is promoted by excess reaction gas.

6. Process according to claim 1, in which aromatic solvents are used as the inert organic solvent.

7. Process according to claim 1, in which chlorobenzene is used as the inert organic solvent.

8. Process according to claim 1, in which halogenated hydrocarbons are used as the inert organic solvent.

9. Process according to claim 1, in which 1,2-dichloroethane is used as the solvent.

10. Process according to claim 4, in which potassium phenolate is used as the base.

11. Process according to claim 4, in which potassium tert.-butylate is used as the base.

12. Process according to claim 4, in which alkali metal hydroxides are used as the bases.

* * * * *